United States Patent [19]

Kühle et al.

[11] Patent Number: 4,514,417

[45] Date of Patent: Apr. 30, 1985

[54] COMBATING FUNGI WITH NEW N-SULPHENYLATED ALLOPHANATES

[75] Inventors: Engelbert Kühle, Bergisch-Gladbach; Hermann Hagemann, Leverkusen; Volker Paul, Solingen; Wilhelm Brandes, Leichlingen, all of Fed. Rep. of Germany

[73] Assignee: Bayer Aktiengesellschaft, Leverkusen, Fed. Rep. of Germany

[21] Appl. No.: 328,318

[22] Filed: Dec. 7, 1981

[30] Foreign Application Priority Data

Dec. 30, 1980 [DE] Fed. Rep. of Germany ....... 3049440

[51] Int. Cl.³ .................... C07C 83/10; A01N 37/00
[52] U.S. Cl. .......................... 514/482; 260/453 RW; 260/455 A
[58] Field of Search ................. 260/455 A, 453 RW; 424/300, 298

[56] References Cited

U.S. PATENT DOCUMENTS 2,910,498 10/1959 Meuly ............................ 260/455 A

OTHER PUBLICATIONS

Chemische Berichte, Nr. 10, 99, Jahrgang, 1966 pp. 3103–3107, 3063.

Primary Examiner—Henry R. Jiles
Assistant Examiner—Robert C. Whittenbaugh
Attorney, Agent, or Firm—Sprung Horn Kramer & Woods

[57] ABSTRACT

N-sulphenylated allophanates of the formula

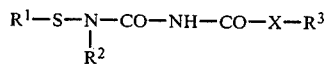

in which
  $R^1$ represents a trihalogenomethyl radical,
  $R^2$ represents an aliphatic, cycloaliphatic, araliphatic or aromatic radical which may in each case be optionally substituted,
  $R^3$ represents an aliphatic, cycloaliphatic, araliphatic or aromatic radical which may in each case be optionally substituted and
  X represents oxygen or sulphur, which possess fungicidal activity.

8 Claims, No Drawings

COMBATING FUNGI WITH NEW N-SULPHENYLATED ALLOPHANATES

The invention relates to certain new N-sulphenylated allophanates, to a process for their preparation and to their use as fungicides.

It has already been known for a long time that N-trihalogenomethylthio compounds can be used as fungicides in agriculture. Thus, for example, N-(trichloromethylthio)-tetrahydrophthalimide and N,N-dimethyl-N'-phenyl-N'-fluorodichloromethylthio)-sulphamide are employed in practice for combating fungal diseases in fruit growing and viticulture (see German Pat. No. 887,506 and Angew. Chem. 76, 807 (1964)). However, their action in tropical crops, for example in rice, is inadequate. The same is true of the zinc salts of alkylene-bis-dithiocarbamic acids, which have also already been known for a long time and otherwise have worldwide importance as fungicides (see, for example, R. Wegler, "Chemie der Pflanzenschutz- und Schädlingsbekämpfungsmittel" ("Chemistry of Plant Protection Agents and Agents for Combating Pests"), Volume 2, page 65, Springer-Verlag, Berlin/Heidelberg/New York (1970)).

The present invention now provides, as new compounds, the N-sulphenylated allophanates of the general formula

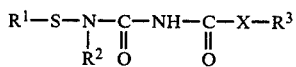 (I)

in which $R^1$ represents a trihalogenomethyl radical, $R^2$ and $R^3$, which may be identical or different, each represent an aliphatic, cycloaliphatic, araliphatic or aromatic radical which may in each case be optionally substituted and X represents oxygen or sulphur.

The invention also provides a process for the preparation of a compound of the general formula (I), in which (a) an isocyanate of the general formula

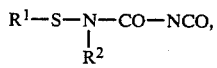 (II)

in which $R^1$ and $R^2$ have the abovementioned meanings, is reacted with a hydroxy or mercapto compound of the general formula

 (III), in which $R^3$ and X have the abovementioned meanings, if appropriate in the presence of a diluent and/or of a catalyst, or (b) a sulphenic acid amide of the general formula

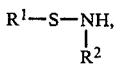 (IV)

in which $R^1$ and $R^2$ have the abovementioned meanings, is reacted with an acyl isocyanate of the general formula

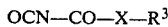 (V), in which $R^3$ and X have the abovementioned meanings, if appropriate in the presence of a diluent and/or of a catalyst.

The N-sulphenylated allophanates of the formula (I) have powerful fungicidal properties.

Surprisingly, the N-sulphenylated allophanates according to the invention exhibit a considerably more powerful fungicidal action, especially in rice crops, than the compounds known from the state of the art. The substances according to the invention thus represent an enrichment of the art.

The formula (I) provides a general definition of the N-sulphenylated allophanates according to the invention. Preferably in this formula, $R^1$ represents trichloromethyl or fluorodichloromethyl, $R^2$ represents an optionally halogenated, saturated or unsaturated aliphatic radical which has up to 6 carbon atoms and can optionally be interrupted by one or more hetero-atoms (such as oxygen or nitrogen); a cycloaliphatic radical with 5 to 8 carbon atoms; an araliphatic radical which has 7 to 10 carbon atoms and of which the aromatic part can optionally carry one or more substituents selected from halogen, nitro groups, trifluoromethyl groups, alkyl groups and alkoxy groups with up to 4 carbon atoms; or an aromatic radical which has 6 to 10 ring carbon atoms and can optionally carry one or more substituents selected from halogen, nitro groups, cyano groups, trifluoromethyl groups and alkyl groups, alkylthio groups and alkoxy groups with in each case up to 4 carbon atoms, and $R^3$ represents an optionally halogenated, saturated or unsaturated aliphatic radical which has up to 8 carbon atoms and can be interrupted by one or more hetero-atoms (such as oxygen and/or sulphur and/or nitrogen); a cycloaliphatic radical which has 5 to 7 carbon atoms and is optionally substituted by alkyl with up to 4 carbon atoms; an araliphatic radical which has 7 to 10 carbon atoms and of which the aromatic part can optionally carry one or more substituents selected from halogen, nitro groups, trifluoromethyl groups and alkyl groups and alkoxy groups with in each case up to 4 carbon atoms; or an aromatic radical which has 6 to 10 ring carbon atoms and can optionally carry one or more substituents selected from halogen, nitro groups, cyano groups, trifluoromethyl groups and alkyl groups, alkylthio groups and alkoxy groups with in each case up to 4 carbon atoms. Very particularly preferred compounds of the general formula (I) are those in which $R^1$ represents trichloromethyl or fluorodichloromethyl, $R^2$ represents an alkyl, alkenyl or halogenoalkyl group with in each case up to 4 carbon atoms, cyclopentyl, cyclohexyl or a benzyl or phenyl radical that optionally carries one or more substituents selected from halogen, nitro groups, methyl groups and trifluoromethyl groups, and $R^3$ represents an alkyl, alkenyl or halogenoalkyl group with in each case up to 4 carbon atoms, cyclopentyl, cyclohexyl or a benzyl or phenyl radical that optionally carries one or more substituents selected from halogen, nitro groups, methyl groups, methoxy groups, methylthio groups, cyano groups and trifluoromethyl groups.

In the preferred and particularly preferred compounds of the formula (I),

X represents oxygen or sulphur.

If, for the preparation of a compound of the formula (I), N-(fluorodichloromethylthio)-N-(methyl)-carbamoyl isocyanate and phenol are used as starting compounds according to process variant (a) or N-(fluorodichloromethylthio)-N-methylamide and phenoxycarbonyl isocyanate are used as starting compounds according to process variant (b), the course of the reaction can be represented by the following equation:

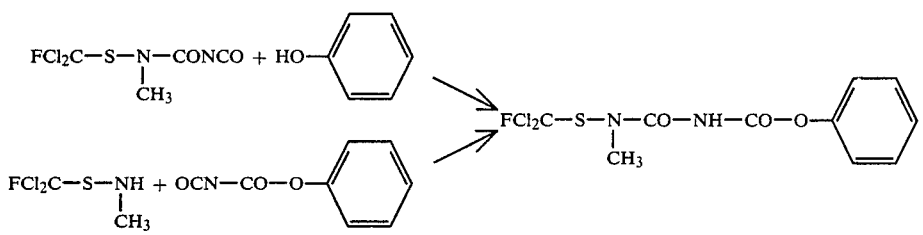

The formula (II) provides a general definition of the isocyanates to be used as starting substances for process variant (a). In this formula, $R^1$ and $R^2$ preferably have those meanings which have already been mentioned as preferred for these substituents in the description of the substances of the formula (I).

The isocyanates of the formula (II) have not previously been described in the literature; they are, however, the subject of German Patent Application P.3049488.5 of 30.12.1980 [Le A 20 570]. They can be prepared by a process in which trihalogenomethanesulphenamides of the general formula

in which $R^1$ and $R^2$ have the abovementioned meanings, are reacted with chlorocarbonyl isocyanate of the formula Cl—CO—NCO (VI), if appropriate in the presence of a diluent, in the temperature range between 0° and 150° c. (see also the preparative examples hereinbelow).

Suitable isocyanates of the formula (II) are the carbonyl-isocyanates of N-(trichloromethylsulphenyl)-, N-fluorodichloromethylsulphenyl)- and N-(trifluoromethyl-sulphenyl)-methylamine, -isopropylamine, -allylamine, -2-methoxyethylamine, -tert.-butylamine, -cyclopentylamine, -cyclohexylamine, -benzylamine, -4-chlorobenzylamine, -phenethylamine, -aniline, -3-trifluoromethylaniline, -3,4-dichloroaniline, -3-anisidine, -3-toluidine, -2-aminopyridine and -2-aminofuran.

The formula (III) provides a definition of the hydroxy or mercapto compounds also required for process variant (a). In this formula, X and $R^3$ preferably have those meanings which have already been mentioned as preferred for these substituents in the description of the compounds of the formula (I).

Suitable compounds of the formula (III) are methanol, ethanol and isopropanol, and also allyl, isobutyl, cyclohexyl, 4-methylcyclohexyl, benzyl, phenethyl and 4-chlorobenzyl alcohol, as well as phenol, 4-chlorophenol, 4-cresol, hydroquinone monomethyl ether, methylmercaptan, butylmercaptan, thiophenol and 4-methylthiophenol.

The compounds of the formula (III) are generally known compounds of organic chemistry.

The formula (IV) provides a general definition of the sulphenic acid amides to be used as starting substances for process variant (b). In this formula, $R^1$ and $R^2$ preferably have those meanings which have already been mentioned as preferred for these substituents in the description of the compounds of the formula (I). The compounds can be obtained by reaction of the corresponding primary amines with trihalogenomethanesulphenic acid chloride, for example in toluene as a solvent, in the temperature range between +20° and 30° C. (see Chem. Abstr. 60, 5519 (1964)).

The formula (V) provides a definition of the acyl isocyanates also required as starting substances for process variant (b). In this formula, X and $R^3$ preferably have those meanings which have already been mentioned as preferred for these radicals in the description of the compounds of the formula (I). The acyl isocyanates of the formula (V) are known, or they can be prepared in a known manner from alcohols, phenols or the corresponding thiol compounds and chlorocarbonyl isocyanate (see Angew. Chem. 89, 789 (1977)). The compounds of the formula (III) listed above can be used as the alcohols and phenols or the corresponding thiol compounds in this reaction.

Possible diluents for the reactions in process variants (a) and (b) are inert organic solvents. These include, as preferences, hydrocarbons, such as benzene or toluene, ethers, such as diethyl ether or tetrahydrofuran, and chlorinated hydrocarbons, such as chloroform or carbon tetrachloride.

For the purpose of a more rapid and a complete course of the reaction, the reactions in process variants (a) and (b) can be carried out in the presence of a basic catalyst, for example an amine. Small amounts of triethylamine are preferably used.

The reaction temperatures can be varied within a substantial range in process variants (a) and (b). In general, the reaction is carried out at between −10° and +100° C., preferably between +10° and 50° C.

In carrying out process variants (a) and (b), 1 mol of the compound of the formula (III) or (V) respectively is employed per mol of the compound of the formula (II) or (IV), respectively. It is expedient for the isocyanates of the formula (II) or the acyl isocyanates of the formula (V) to be initially introduced and for the compounds of the formula (III) (in the case of process variant (a)) or of the formula (IV) (in the case of process variant (b)) to be added, with stirring. The end products are isolated in the generally customary manner; the end products are in most cases non-distillable oils or crystals.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Pyricularia oryzae, the causative organism of Brusone disease, and Pellicularia sasakii, the causative organism of leaf sheath blight in rice. Good successes are also achieved against grey mould (Botrytis cinerea) and against apple scab (Venturia inaequalis).

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal-phthalocyanine dyestuffs, and trace nutrients such as salts or iron, manganese, boron, copper, cobalt, molybdenum and zinc.

The formulations in general contain from 0.1 to 95 percent by weight of active compound, preferably from 0.5 to 90 percent.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of, in general, 0.001 to 50 g, preferably 0.01 to 10 g, are employed per kilogram of seed.

For the treatment of soil, active compound concentrations of, in general, 0.00001 to 0.1% by weight, preferably 0.0001 to 0.02%, are employed at the place of action.

The present invention also provides a fungicidal composition containing as active ingredient a compound of the present invention in admixture with a solid or liequefied gaseous diluent or carrier or in admixture with a liquid diluent or carrier containing a surface-active agent.

The present invention also provides a method of combating fungi which comprises apply to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(Process variant (b))

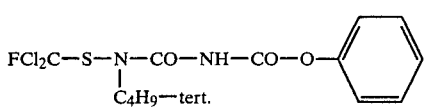
(1)

62 g (0.3 mol) of N-(fluorodichloromethanesulphenyl)-N-tert.-butylamide (boiling point 60°–65° C./13 mm Hg), which had been prepared from fluorodichloromethanesulphenyl chloride and tert.-butylamine and was dissolved in 30 ml of toluene, were added dropwise at room temperature to 48.8 g (0.3 mol) of phenoxycarbonyl isocyanate, dissolved in 150 ml of dry toluene. During this addition, the temperature rose to 44° C. After the mixture had cooled, 39 g of N-(fluorodichloromethanesulphenyl)-N-(tert.-butyl)-allophanic acid phenyl ester of melting point 101° to 102° C. crystallized out. A further 34 g of the reaction product could be obtained from the mother liquor by the addition of petroleum ether. A total of 73 g of the compound mentioned were thus obtained, and the yield was 66% of theory.

EXAMPLE 2

(Process variant (b))

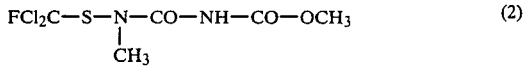
(2)

8.2 g (0.05 mol) of fluorodichloromethanesulphenyl-methylamide were added dropwise to a solution of 5 g (0.05 mol) of methoxycarbonyl isocyanate in 100 ml of dry toluene. During this addition, the temperature rose to about 35° C. After the reaction had subsided, the mixture was concentrated in vacuo. The residue (12 g) was recrystallized from ligroin. 10 g of N-(fluorodichloromethanesulphenyl)-N-(methyl)-allophanic acid methyl ester of melting point 74°–76° C. were thereby obtained, that is to say 76% of theory.

EXAMPLE 3

(a) Chlorocarbonyl isocyanate required as starting material is known from the literature (see Angew. Chem. 89, 789 (1977) and is described in detail. The addition product of phosgene and cyanogen chloride was first prepared on an active charcoal catalyst and the adduct was then hydrolysed with methanesulphonic acid, chlorocarbonyl isocyanate being obtained in 90% yield.

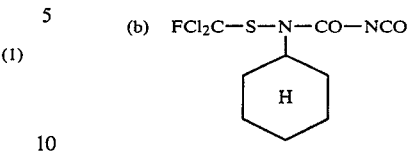

A solution of 45 g (0.2 mol) of fluorodichloromethanesulphenyl-N-(cyclohexyl)-amide (boiling point 68° to 70° C./0.1 mm Hg) in 50 ml of chlorobenzene was added dropwise to a solution of 44 g (0.4 mol) of chlorocarbonyl isocyanate in 150 ml of chlorobenzene at +10° to 20° C., with ice-cooling. The reaction solution was then heated gradually to the boiling point, hydrogen chloride being split off at from about 70°–80° C. The mixture was kept at the reflux temperature for 1 hour, the solution was concentrated in vacuo and the residue was distilled. 46 g of N-(fluorodichloromethane-sulphenyl)-N-(cyclohexyl)-amido-carbonyl isocyanate of boiling point 158° to 160° C./11 mm Hg were obtained. The yield was 76% of theory.

Process variant (a)

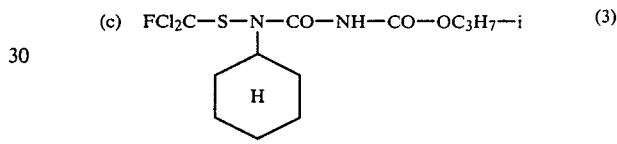
(3)

10 ml of isopropanol, with which a few drops of triethylamine were mixed, were added dropwise to a solution of 15 g (0.05 mol) of N-(fluorodichloromethanesulphenyl)-N-(cyclohexyl)-amido-carbonyl isocyanate (boiling point 158°–160° C./11 mm Hg) in 100 ml of toluene. During this addition, the temperature rose to about 33° C. The mixture was subsequently stirred for a while and was concentrated in vacuo. The reaction product was obtained in the form of an oil with a refractive index $n_D^{20}$ of 1.4975. The yield was quantitative.

The following compounds of the general formula

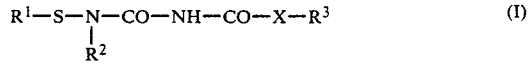
(I)

were obtained in a manner corresponding to that described in Example 1, 2 or 3.

TABLE

| Compound No. | $R^1$ | $R^2$ | $XR^3$ | Melting point (°C.) or refractive index |
|---|---|---|---|---|
| 4 | $FCl_2C$ | $C_3H_7$—i | —O—⟨phenyl⟩ | $n_D^{20} = 1.5379$ |
| 5 | $FCl_2C$ | —⟨cyclohexyl-H⟩ | —O—⟨phenyl⟩ | $n_D^{20} = 1.5389$ |

TABLE-continued

| Compound No. | R¹ | R² | XR³ | Melting point (°C.) or refractive index |
|---|---|---|---|---|
| 6 | Cl₃C | cyclohexyl-H | O-phenyl | $n_D^{20} = 1.5570$ |
| 7 | FCl₂C | cyclohexyl-H | O-(4-Cl-phenyl) | 129–130 |
| 8 | FCl₂C | CH₃ | O-phenyl | 100–102 |
| 9 | FCl₂C | CH₃ | S—C₄H₉—n | 69–70 |
| 10 | FCl₂C | C₃H₇—i | O—CH₃ | $n_D^{20} = 1.4983$ |
| 11 | FCl₂C | cyclohexyl-H | S—C₃H₇—n | 91–94 |
| 12 | Cl₃C | C₃H₇—i | S—C₃H₇—n | 70–72 |
| 13 | Cl₃C | C₄H₉—n | S—C₃H₇—n | $n_D^{20} = 1.5392$ |
| 14 | FCl₂C | CH₃ | O—CH₂—CF₃ | 55–59 |
| 15 | FCl₂C | CH₃ | S-phenyl | 70–72 |
| 16 | FCl₂C | C₄H₉—t | O—C₃H₇—i |  |
| 17 | FCl₂C | CH₃ | O-cyclohexyl-H | 105–107 |
| 18 | FCl₂C | C₂H₅ | O-cyclohexyl-H | 65–67 |
| 19 | FCl₂C | C₃H₇—n | O-cyclohexyl-H | $n_D^{20} = 1.5029$ |
| 20 | FCl₂C | C₃H₇—i | O-cyclohexyl-H | 68–70 |
| 21 | FCl₂C | CH₂—CH=CH₂ | O-cyclohexyl-H | 62–63 |
| 22 | FCl₂C | C₄H₉—n | O-cyclohexyl-H | $n_D^{20} = 1.5020$ |

TABLE-continued

| Compound No. | R¹ | R² | XR³ | Melting point (°C.) or refractive index |
|---|---|---|---|---|
| 23 | FCl$_2$C | C$_4$H$_9$—i | O—cyclohexyl (H) | 70–72 |
| 24 | FCl$_2$C | C$_4$H$_9$—t | O—cyclohexyl (H) | n$_D^{20}$ = 1.5038 |
| 25 | FCl$_2$C | CH$_3$ | O—C$_6$H$_4$—Cl | 113–114 |
| 26 | FCl$_2$C | C$_2$H$_5$ | O—C$_6$H$_4$—Cl | 110–112 |
| 27 | FCl$_2$C | C$_3$H$_7$—n | O—C$_6$H$_4$—Cl | 102–104 |
| 28 | FCl$_2$C | C$_3$H$_7$—i | O—C$_6$H$_4$—Cl | 105 |
| 29 | FCl$_2$C | CH$_2$—CH=CH$_2$ | O—C$_6$H$_4$—Cl | 78–80 |
| 30 | FCl$_2$C | C$_4$H$_9$—n | O—C$_6$H$_4$—Cl | 77–79 |
| 31 | FCl$_2$C | C$_4$H$_9$—i | O—C$_6$H$_4$—Cl | 83–85 |
| 32 | FCl$_2$C | C$_4$H$_9$—t | O—C$_6$H$_4$—Cl | 89–92 |
| 33 | FCl$_2$C | C$_3$H$_7$—i | O—C$_6$H$_4$—OCH$_3$ | n$_D^{20}$ = 1.5365 |
| 34 | FCl$_2$C | C$_4$H$_9$—i | O—C$_6$H$_4$—OCH$_3$ | 76–80 |
| 35 | FCl$_2$C | C$_4$H$_9$—t | O—C$_6$H$_4$—OCH$_3$ | 115–120 |

TABLE-continued

| Compound No. | R¹ | R² | XR³ | Melting point (°C.) or refractive index |
|---|---|---|---|---|
| 36 | $FCl_2C$ | $C_3H_7$—i | S—⬡ | 75–78 |
| 37 | $FCl_2C$ | $C_4H_9$—i | S—⬡ | 89–90 |
| 38 | $FCl_2C$ | $C_4H_9$—t | S—⬡ | 82–85 |
| 49 | $FCl_2C$ | $C_3H_7$—i | S—⬡—Cl | 98–99 |
| 40 | $FCl_2C$ | $C_4H_9$—i | S—⬡—Cl | 77–80 |
| 41 | $FCl_2C$ | $C_4H_9$—t | S—⬡—Cl | 109–112 |
| 42 | $FCl_2C$ | ⬡— | $OCH_3$ | $n_D^{20} = 1.5618$ |

USE EXAMPLES

The fungicidal activity of the compounds of this invention is illustrated by the following examples wherein the compounds according to the present invention are each identified by the number (given in brackets) from Examples 1 to 3 and the table hereinabove.

The compound given below was used as the comparison substance in the examples which follow:

(A)

EXAMPLE 4

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for protective activity, young rice plants were sprayed with the preparation of active compound until dripping wet. After the spray coating had dried off, the plants were inoculated with an aqueous spore suspension of Pyricularia oryzae. The plants were then placed in a greenhouse at 100% relative atmospheric humidity and 25° C.

Evaluation of the disease infestation was carried out 4 days after the inoculation.

In this test, a clearly superior activity compared with the prior art was shown, for example, by the compounds (42), (9) and (5).

EXAMPLE 5

Pellicularia test (rice)
Solvent: 12.5 parts by weight of acetone
Emulsifier: 0.3 part by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for activity, young rice plants in the 3 to 4 leaf stage were sprayed until dripping wet. The plants remained in a greenhouse until they had dried off. The plants were then inoculated with Pellicularia sasakii and were placed in a greenhouse at 25° C. and 100% relative atmospheric humidity.

The evaluation of the disease infestation was carried out 5–8 days after the inoculation.

15

In this test, a clearly superior activity compared with the prior art was shown, for example, by the compounds (42), (9) and (5).

EXAMPLE 6

Botrytis test (beans)/protective
Solvent: 4.7 parts by weight of acetone
Dispersing agent: 0.3 part by weight of alkylaryl polyglycol ether
Water: 95 parts by weight The amount of active compound required to give the desired concentration of active compound in the spray liquid was mixed with the stated amount of the solvent and the concentrate was diluted with the stated amount of water which contained the stated additive.

Phaseolus vulgaris plants in the 2-leaf stage were sprayed with the spray liquid until dripping wet. After 24 hours, 2 small pieces of agar covered with Botrytis cinerea were placed on each leaf. The inoculated plants were placed in a darkened, moist chamber at 20° C. 3 days after the inoculation, the size of the infected spots on the leaves was rated.

The ratings were converted into percent infection. 0% denoted no infection and 100% denoted that the plants were completely infected.

In this test, a clearly superior activity compared with the prior art was shown, for example, by the compound (9).

It will be understood that the specification and examples are illustrative but not limitative of the present invention and that other embodiments within the spirit and scope of the invention will suggest themselves to those skilled in the art.

What is claimed is:

1. A N-sulphenylated allophanate of the formula

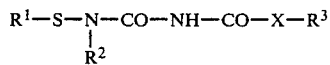

in which
R$^1$ represents trichloromethyl or fluorodichloromethyl,
R$^2$ represents an optionally halogenated, saturated or unsaturated aliphatic radical which has up to 6 carbon atoms and can optionally be interrupted by one or more nitrogen and oxygen atoms; a cycloaliphatic radical with 5 to 8 carbon atoms; a lower hydrocarbyl araliphatic radical which has 7 to 10 carbon atoms and of which the aromatic part can optionally carry cyano groups, nitro groups, trifluoromethyl groups, alkyl and alkoxy groups with up to 4 carbon atoms; or a phenyl radical which can optionally carry one or more substituents selected from halogen, nitro groups, cyano groups, trifluoromethyl groups and alkyl groups, alkylthio groups and alkoxy groups with in each case up to 4 carbon atoms, and
R$^3$ represents an optionally halogenated, saturated or unsaturated aliphatic radical which has up to 8 carbon atoms and can be interrupted by one or more nitrogen, oxygen and sulphur atoms; a cycloaliphatic radical which has 5 to 7 carbon atoms and is optionally substituted by alkyl with up to 4 carbon atoms; a phenylalkyl radical of which the phenyl part can optionally carry one or more substituents selected from halogen, cyano groups, nitro groups, trifluoromethyl groups and alkyl groups, alkylthio and alkoxy groups with in each case up to 4 carbon atoms; or a phenyl radical which can optionally carry one or more substituents selected from halogen, nitro groups, cyano groups, trifluoromethyl groups and alkyl groups, alkylthio groups and alkoxy groups with in each case up to 4 carbon atoms, and
X represents oxygen or sulphur.

2. A compound according to claim 1, in which
R$^1$ represents trichloromethyl or fluorodichloromethyl,
R$^2$ represents an alkyl, alkenyl or halogenoalkyl group with in each case up to 4 carbon atoms, cyclopentyl, cyclohexyl, or a benzyl or phenyl radical that optionally carries one or more substituents selected from halogen, nitro groups, methyl groups and trifluoromethyl groups, and
R$^3$ represents an alkyl, alkenyl or halogenoalkyl group with in each case up to 4 carbon atoms, cyclopentyl, cyclohexyl, or a benzyl or phenyl radical that optionally carries one or more substituents selected from halogen, nitro groups, methyl groups, methoxy groups, methylthio groups, cyano groups and trifluoromethyl groups.

3. A compound according to claim 1, wherein such compound is N-(fluorodichloromethanesulphenyl)-N-(cyclohexyl)-allophanic acid phenyl ester of the formula

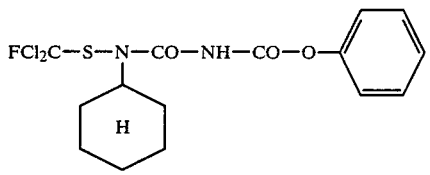

4. A compound according to claim 1, wherein such compound is N-(fluorodichloromethanesulphenyl)-N-(methyl)-allophanic acid n-thiobutyl ester of the formula

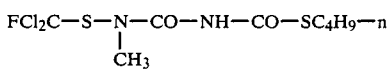

5. A compound according to claim 1, wherein such compound is N-(fluorodichloromethanesulphenyl)-N-(phenyl)-allophanic acid methyl ester of the formula

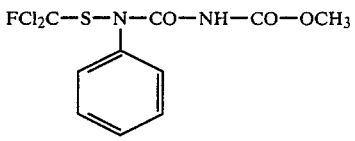

6. A fungicidal composition comprising a fungicidally effective amount of a compound according to claim 1 in admixture with a diluent.

7. A method of combating fungi comprising applying to the fungi, or to a habitat thereof, a fungicidally effective amount of a compound according to claim 1.

8. The method according to claim 7, wherein such compound is
N-(fluorodichloromethanesulphenyl)-N-(cyclohexyl)-allophanic acid phenyl ester,
N-(fluorodichloromethanesulphenyl)-N-(methyl)-allophanic acid n-thiobutyl ester or
N-(fluorodichloromethanesulphenyl)-N-(phenyl)-allophanic acid methyl ester.

* * * * *